(12) United States Patent
Gaitas et al.

(10) Patent No.: US 8,394,625 B2
(45) Date of Patent: Mar. 12, 2013

(54) LAB-ON-A-PIPETTE

(76) Inventors: Angelo Gaitas, Ann Arbor, MI (US); Amar Basu, Novi, MI (US)

( * ) Notice: Subject to any disclaimer, the term of this patent is extended or adjusted under 35 U.S.C. 154(b) by 0 days.

(21) Appl. No.: 13/099,351

(22) Filed: May 2, 2011

(65) Prior Publication Data

US 2011/0269121 A1      Nov. 3, 2011

Related U.S. Application Data

(60) Provisional application No. 61/330,362, filed on May 2, 2010.

(51) Int. Cl.
*C12M 1/00* (2006.01)
*B01L 3/02* (2006.01)
*G01N 21/00* (2006.01)

(52) U.S. Cl. ............... 435/283.1; 435/288.2; 435/288.7; 422/68.1; 422/82.05; 422/501; 422/514; 977/701; 977/704; 977/724; 977/725

(58) Field of Classification Search .......................... None
See application file for complete search history.

(56) References Cited

U.S. PATENT DOCUMENTS

| 6,458,545 B2 * | 10/2002 | Tanaami | 435/6.11 |
| 2008/0014573 A1 * | 1/2008 | Nagamura | 435/4 |
| 2008/0176755 A1 * | 7/2008 | Amundson et al. | 506/7 |

FOREIGN PATENT DOCUMENTS

WO    WO2010/012423    * 2/2010

* cited by examiner

*Primary Examiner* — Betty Forman

(57) ABSTRACT

This invention generally relates to an integrated 'lab-on-a-Pipette'™ which will provide sample-to-answer single cell genetic diagnosis for preimplantation genetic diagnosis (PGD) and other forms of single cell analysis (SCA). SCA is a quickly growing field with substantial impact in prenatal testing, cancer biopsies, diabetes, stem cell research, and our overall understanding of heterogeneity in biology. However, single cell genetic analysis is challenging, inaccurate, and in many cases impossible, due to the small amount of sample (5 pg), and difficulties in handling small sample volumes (50-100 pL). The 'lab-on-a-pipette' device integrates a microaspiration tip with microfluidic analysis components to conduct in-situ, real-time single cell genetic diagnosis in a single device. The microaspiration tip extracts and encapsulate a cell into an ultra-low volume plug (~300 pL).

1 Claim, 5 Drawing Sheets (a) side view (b) bottom view of design 1

(c) bottom view of design 2

(d) bottom view of design 3

LAB-ON-A-PIPETTE

CROSS REFERENCE TO RELATED APPLICATIONS

This application claims priority from U.S. Provisional Patent Application Ser. No. 61/330,362, entitled "LAB-ON-A-PIPETTE", filed on 2 May 2010. The benefit under 35 USC §119(e) of the United States provisional application is hereby claimed, and the aforementioned application is hereby incorporated herein by reference.

SEQUENCE LISTING OR PROGRAM

Not Applicable

FEDERALLY SPONSORED RESEARCH

Not Applicable

TECHNICAL FIELD OF THE INVENTION

This invention relates to an integrated 'lab-on-a-Pipette'™ device (the device) which will provide sample-to-answer single cell genetic diagnosis for preimplantation genetic diagnosis (PGD) and other forms of single cell analysis (SCA). SCA is a quickly growing field with substantial impact in prenatal testing, cancer biopsies, diabetes, stem cell research, and our overall understanding of heterogeneity in biology. However, single cell genetic analysis is challenging, inaccurate, and in many cases impossible, due to the small amount of sample (5 pg), and difficulties in handling small sample volumes (50-100 µL). The 'lab-on-a-pipette' device integrates a microaspiration tip with microfluidic analysis components to conduct in-situ, real-time single cell genetic diagnosis in a single disposable device. The microaspiration tip extracts and encapsulates a cell into an ultra-low volume plug (~300 µL).

BACKGROUND OF THE INVENTION

This invention relates to an integrated 'lab-on-a-pipette' which will provide sample-to-answer single cell genetic diagnosis for preimplantation genetic diagnosis (PGD) and other forms of single cell analysis (SCA). SCA is a quickly growing field with substantial impact in prenatal testing, cancer biopsies, diabetes, stem cell research, and our overall understanding of heterogeneity in biology. However, single cell genetic analysis is challenging, inaccurate, and in many cases impossible, due to the small amount of sample (5 pg), and difficulties in handling small sample volumes (50-100 µL). The 'lab-on-a-pipette' device integrates a microaspiration tip with microfluidic analysis components to conduct in-situ, real-time single cell genetic diagnosis in a single disposable device. The microaspiration tip will extract and encapsulate a cell into an ultra-low volume plug (~300 µL). The microfluidic analysis module, which includes a microheater and embedded lyophilized reagents, will perform cell lysis, polymerase chain reaction (PCR) amplification, and real-time fluorescence analysis. This solution is novel, simple (requires no integrated valves), and builds upon well established technologies for a high likelihood of success. Microfluidic devices have been successfully used to analyze low copy biomolecules (less than 1 pg) such as DNA from a single cell. Glass micropipettes are regularly used to extract single cells. Combining the two components in a single integrated system provides an elegant solution the to the difficult problem of single cell sampling and isolation. It addresses major limitations of the current preimplantation genetic diagnosis (PGD) procedures by providing a 'one-tube' solution to extract and analyze a single cell for genetic mutations. This eliminates fluid transfers (which cause contamination), reduces analysis time, and reduces operator and reagent costs. Moreover, the small fluid volumes (pL) used in the system increases the effective concentration of the sample, and therefore provides better amplification and improved accuracy when measuring single gene mutations. Beyond PGD, the system provides a versatile platform tool for basic research, drug discovery, and clinical diagnosis of rare or localized cell populations.

This technology can greatly improve the accuracy and reduce the costs associated with preimplantation genetic diagnosis (PGD), which will ultimately lead to healthier embryos for at-risk parents conceiving via in vitro fertilization (1% of births per year in the USA). This technology also addresses significant research challenges in single cell analysis (SCA), which relies on microscale technologies to quantiatively analyze the genome, transciptome, and metabolome of a single cell, leading to a greater understanding of heterogenaity in biology. SCA is a young but growing field which has direct implications in cancer diagnostics, undersanding diabetes and immune disorders, stem cell research, and the discovery of new drugs.

IVF is widely used today. More than 1 million children worldwide to date and about 1% of births/year in the US, i.e. more than 45,000/year, have been conceived by IVF (Goldberg). Typically, the embryo quality is assessed using light microscopy where morphological parameters such as fragmentation, number and size of blastomeres, and the nucleus status are evaluated. PGD can be used for prenatal diagnosis of known heritable chromosomal abnormalities or gene mutations (Shulman).

PGD has been used in thousands of IVF clinical cases worldwide since its inception in 1988. In PGD one cell from an in vitro embryo is extracted and biopsied, and this can be performed at different stages. Blastomere biopsy of a 6 to 8-cell embryo is performed on day 3 of IVF and involves two steps: first mechanical (razor, laser) or chemical (enzymatic) interruption of the zona pellucida and then aspiration of a blastomere (the cell produced during cleavage of a fertilized egg) with a biopsy pipette (35 µm diameter) on a manipulator (SCIENTIFIC) (Shulman) (Handyside) while another pipette on a second manipulator is holding the embryo. The procedure typically requires two embryologists. The blastomere with a visible nucleus close to the hole is targeted (SCIENTIFIC). The blastomer does not have to be completely aspirated into the pipette. The aspirated blastomere is then examined. If it has a clear nucleus and is not lysed it is transfered in PCR tubes with 5 µL of lysis buffer for molecular genetics (SCIENTIFIC).

However, blastomere biopsy's limitations decrease the likelihood of an accurate diagnosis (Shulman) (Gleicher). Limitations include: (a) Loss of viable cells (7 to 10%) due to critical steps in cell fixation for nucleate extraction (Velilla) (Shulman). (b) Contamination by ambient DNA due to contamination from extraneous sperm attached to the zona pellucida, carry-over contamination from products of former PCR reactions, DNA in reagents, or operator DNA (Shulman) (Yap) (Thornhill) (Jeanine Cieslak-Janzen) (Rechitsky) (Carson). Contamination is more disastrous than other failures, because it could allow an affected embryo to be implanted by providing a false negative (Shulman). (c) Small amount of DNA (~5 pg) obtained from a single cell is often not sufficient for the diagnosis using current techniques (Shulman). Nested primer PCR improves allele dropout (ADO) rates; but it has a failure rate approaching 10% with one major reason being the loss of nucleic material prior to the process (Shulman).

The "lab-on-a-pipette" device integrates a micro-syringe with a lab-on-a-chip device to conduct in-situ, real-time, immediate single cell genetic diagnosis. The device will interrupt the zona pellucida, extract a cell, and perform PCR (including encapsulation, lysing, adding PCR buffer, thermal cycling, and analysis of the lysate). Microfluidic devices have been successfully used to analyze low copy biomolecules (less than 1 pg) such as DNA in a single cell (Huang) (Marcus). Microfluidic platforms have been able to manipulate cells and have provided extremely high detection sensitivity (Huang). However, they have never been combined with micromachined pipettes in a single system for in-situ diagnosis. The device addresses major limitations of the current PGD procedures by being able to analyze small amounts of DNA, eliminating cell fixation and most sources of contamination (since the cell is transferred directly from the embryo to the device for analysis), and reducing costs (less people involved in genetic diagnosis, reduced procedures and time).

For time sensitive analysis like PGD, fast analysis rates are very important. This device can complete an analysis much faster. There is no need for instance to transfer the cells to different tubes and ship the cells to a different location for analysis. In addition, amplification can be done much faster, embedded micro-heaters can heat to 100° C. in less than 10 seconds, reducing the time that it takes to complete 30 cycles to a couple of minutes from the current 10 minutes. The smaller fluid volumes in the form of plug handled by our micropipette and microfluidic device increase the effective concentration and provide better amplification with improved results and better chances of measuring single gene mutations.

On a broader scope, the lab-on-a-pipette technology can potentially become a versatile tool for the exploding field of single cell analysis (SCA). SCA is used to study heterogeneity in cell populations and in practical situations where only low cell counts are available (forensics, cancer diagnostics, and stem cell research) (Anselmetti). SCA tools are urgently needed to quantitatively record proteomic, genomic, or metabolic markers which reveal the status of the cell. Low-copy-number biomolecules (<1000 molecules/cell) have a significant function in cell operation, including signaling and regulation of gene expression (Ying), although they are often lost in the detection process and not analyzed (Gygi). Small changes of concentration or altered modification patterns of disease-relevant low abundance components can be potentially used as markers of different stages of disease such as cancer, in diagnosis, in monitoring the growth of the tumor, and response to the therapy. Molecular alterations can be used to identify cancer, determine malignancy grade, enhance diagnosis and prognosis in cancers, and clinical response to therapy (Maruvada). SCA is also important in studying cell mutations due to environmental changes, drug screening, and provides an alternative in the event of regulatory changes such as the ban on animal testing in the European Union (EU). Understanding the molecular origin of disease allows for direct treatment and the capability to predict and prevent disease. This system can detect low concentration of biomolecules such as DNA. This provides a versatile platform tool for basic research, drug discovery, and clinical diagnosis of rare or localized cell populations.

This tool can be broadly used by the research and medical community for genetic diagnosis as a fully functioning and automated single cell genetic analysis "sample-to-answer" system. The lab-on-a-pipette fills the deficiency gap for these conditions in the prior art.

SUMMARY OF THE INVENTION

This invention generally relates to an integrated 'lab-on-a-pipette' which will provide "sample-to-answer" single cell genetic diagnosis for preimplantation genetic diagnosis (PGD) and other forms of single cell analysis (SCA). "In Vitro Fertilization" (IVF) has led to over 1 million births worldwide to date and accounts for about 1% of births/year in the US, i.e. more than 45,000/year (Goldberg). IVF patients who are carriers of heritable genetic diseases request PGD of known heritable chromosomal abnormalities or gene mutations (Shulman). In PGD, a single cell is extracted from an in vitro 3-day embryo (6-8 cells), lysed, and subjected to PCR amplification for genetic analysis (Handyside) (A. K. Handyside) (Clement-Sengewald). Despite the many well developed approaches, blastomere biopsy/PGD is expensive, time consuming, requires skilled operators, and has several limitations which decrease the likelihood of an accurate diagnosis (Shulman) (Gleicher). Limitations include: (a) Loss of viable cells (7 to 10%) due to critical steps in cell fixation for nucleate extraction (Velilla) (Shulman); (b) Contamination by ambient DNA (Shulman) (Yap) (Thornhill) (Jeanine Cieslak-Janzen) (Rechitsky) (Carson); and (c) PCR failure or misdiagnosis due to the small amount of DNA (~5 pg) obtained from a single cell (Shulman) (Piyamongkol).

This system addresses these challenges. The 'lab-on-a-pipette' device integrates a microaspiration tip with microfluidic analysis components to conduct in-situ, real-time single cell genetic diagnosis in a single disposable device. The microaspiration tip will extract and encapsulate a cell into an ultra-low volume plug. The microfluidic analysis module with embedded lyophilized reagents will perform cell lysis, PCR amplification, and real time fluorescence analysis. Our solution is novel and yet builds upon well established technologies. Microfluidic devices have been successfully used to analyze low copy biomolecules (less than 1 pg) such as DNA of a single cell (Huang) (Marcus) (Liu) (Liu 2). Moreover, microfluidic platforms have been able to manipulate cells and have provided extremely high detection sensitivity (Huang). However, sampling single cells has been a major challenge (Andersson). We couple micromachined aspiration tips directly to sensitive microfluidic analysis modules, providing an elegant solution to the difficult problem of single cell sampling and isolation. The device addresses major limitations of the current PGD procedures by being able to analyze small amounts of DNA, eliminating fluid transfers which cause contamination, reducing analysis time, and reducing costs. Furthermore, the small fluid volumes (pL) used in our system will increase the effective concentration and therefore provide better PCR amplification (Oda) (Lee) (Nagai) and therefore will improved accuracy in measuring single gene mutations.

On a broader scope, the lab-on-a-pipette technology can potentially become a versatile tool for the exploding field of single cell analysis (SCA). SCA tools are urgently needed to quantitatively record proteomic, genomic, or metabolic markers which reveal the status of the cell. Low-copy-number biomolecules (<1000 molecules/cell) have a significant function in cell operation (Ying), although they are often lost in the detection process (Gygi). Small changes of concentration or altered modification patterns of disease-relevant low abundance components can be potentially used as markers of different stages of disease such as cancer, in diagnosis, in monitoring the growth of the tumor, and response to the therapy (Maruvada). SCA is also important in studying cell mutations and in drug screening. The system provides a versatile platform tool for basic research, drug discovery, and clinical diagnosis of rare or localized cell populations. These and other features of the present invention will become obvious to one skilled in the art through the description of the drawings, detailed description of the invention, and the appended claims.

DETAILED DESCRIPTION OF THE INVENTION

Figure 1:
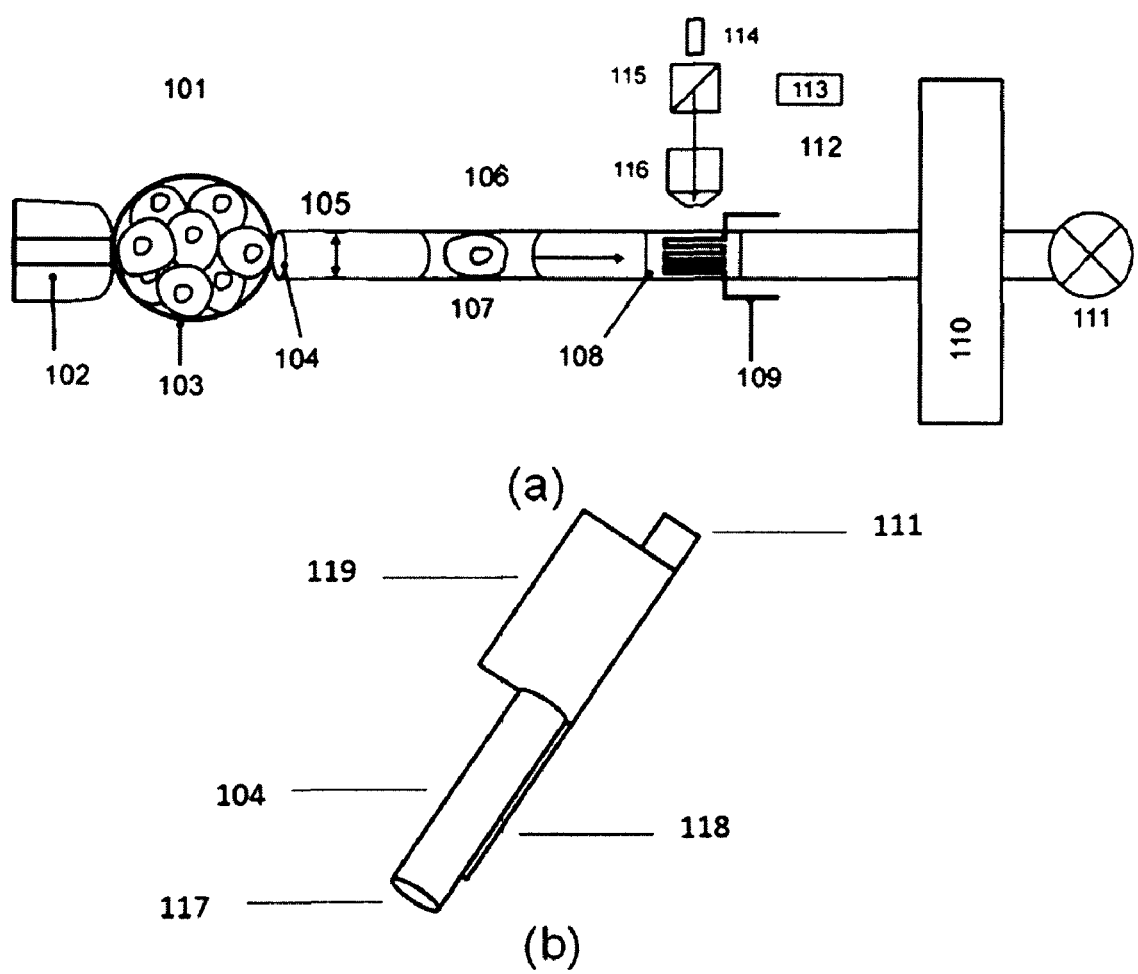
FIGS. 1(a) and 1(b) are schematics of the lab-on-a-pipette system.

The object of the present invention is to provide a device and method for an 'lab-on-a-pipette' device that integrates a microaspiration tip with microfluidic analysis components to conduct in-situ, real-time single cell genetic diagnosis in a single device. The device for analyzing an analyte from a sample, comprises of an elongated hollow structure with an opening at the distal end to extract the analyte, and an analysis module for analyzing the analyte at the proximal end, a positioning device to manipulate the hollow structure and the analysis module near the analyte.

Referring now to the drawings, more particularly to FIG. 1a, which shows a 'lab-on-a-pipette' device. In FIG. 1a: a 101 IVF Petri Dish contains an 103 6-8 Cell Embryo is held by a 102 Holding Pipette. A 104 Micro Aspiration Tip with a 105 40 μm diameter extracts an 106 Encapsulated Single Cell. The cell is encapsulated by a 107 300 pL plug. The lab contains an 108 Embedded Lysis and PCR Reagents (Lypholized), a 109 Microheater for PCR Cycling. The pipette is controlled by a 110 Micromanipulator. A 111 Precision Suction Pump is also used. The detection system also contains a 112 LIF Detector (Off Chip), 113 PMT, 114 Laser, 115 Filter Cube, and 116 Obj. The microaspiration tip will extract and encapsulate a cell into an ultra-low volume plug. The microfluidic analysis module with embedded lyophilized reagents will perform cell lysis, PCR amplification, and real time fluorescence analysis. Our solution is novel and yet builds upon well established technologies. Microfluidic devices have been successfully used to analyze low copy biomolecules (less than 1 pg) such as DNA of a single cell (Huang) (Marcus) (Liu) (e. a. Liu). Moreover, microfluidic platforms have been able to manipulate cells and have provided extremely high detection sensitivity (Huang). However, sampling single cells has been a major challenge (Andersson). We couple micromachined aspiration tips directly to sensitive microfluidic analysis modules, providing an elegant solution to the difficult problem of single cell sampling and isolation. The proposed device addresses major limitations of the current PGD procedures by being able to analyze small amounts of DNA, eliminating fluid transfers which cause contamination (the cell is transferred directly for analysis), reducing analysis time, and reducing costs (less people involved in genetic diagnosis, reduced procedures and time, elimination of expensive hardware). Furthermore, the small fluid volumes (pL) used in our system will increase the effective concentration and therefore provide better amplification and improved accuracy in measuring single gene mutations.

To date, more than 1 million children worldwide have been conceived by IVF, and IVF accounts for 1% of births/year in the US, i.e. more than 45,000/year (Goldberg). PGD is used for prenatal diagnosis of known heritable chromosomal abnormalities or gene mutations (Shulman). As PGD becomes more reliable and inexpensive it will be more prevalent. Ultimately it could be used by the majority of parents who prefer IVF. This technology will also find clinical applications in cancer diagnostics. Fine needle aspiration is regularly used to biopsy tumors, and the ability to perform genetic diagnosis in situ could greatly improve the ability to find the cause and origin of the tumor cell. The capability of single cell analysis could lead to widespread commercialization for clinical use.

FIG. 1b shows a more generalized version of the system that includes a tip with an opening 117 and a pipette 104. The opening 117 could range from a few micron in diameter to a few nanometers depending on the application. For example the opening 117 could be 1 micron in diameter. The pipette includes a sensing and/or actuating element 118. For example, element 118 could be a piezoelectric or piezoresistive element to sense movement or displacement of the pipette. These elements can be added to the pipette on each side to sense up and down movement as well as left and right movement. These elements could also move the pipette. For example a piezoelectric element could be used to move the pipette. A sensing element could also be used to image a surface by measuring the displacement of the pipette in the Z-axis (up and down, out of place direction). A sensing element could also be used to measure the elasticity (the stiffness) of a sample like a cell to determine how hard or how soft it is. The analysis unit 119 (or lab-on-chip) attached to the pipette could include any of the following processes/methods/devices/techniques by themselves or in combination: a fluorescent in situ hybridization (FISH), a polymerase chain reaction (PCR) amplification, a whole genome amplification, a comparative genomic hybridization, a pre-implantation genetic diagnosis, micro-cantilever based detection (explained in paragraph 40), cell lysis, and real time fluorescence analysis. The analysis unit 119 may include any other type of process/method/device/technique that can be used to analyze a biological sample such as a cell, part of a cell, protein, DNA, organelle etc. Pumping 111 to draw the analytes in the microfluidic analysis system may be achieved with a simple syringe operated manually, or with a micro-pump (i.e. a small micromachined pump of dimension comparable to the analysis unit), or with any other type of pumping system capable to producing sufficient suction to draw the analytes in the microfluidic system. The device of FIG. 1 can be powered by any means including but not limited to: batteries, AC power supply etc.

Figure 2:
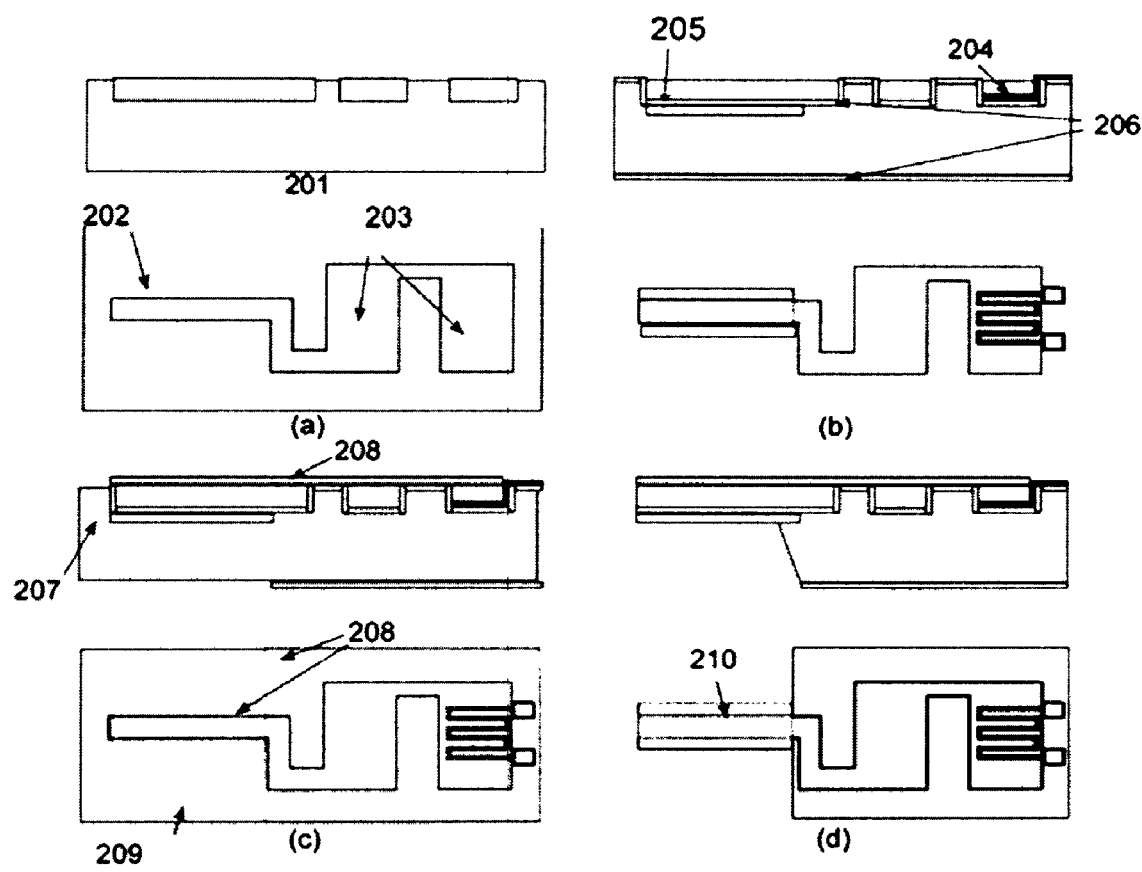
FIG. 2 shows the microfabrication process for the lab-on-a-pipette chip with integrated sampling probe.

FIG. 2 show the fabrication process involves: a) forming trenches and cavities on silicon using deep RIE (201 silicon substrate, 202 trench for sampling, 203 channels for microfluidic components); b) selectively and heavily doping the sampling probe region on the silicon substrate, growing a thermal oxide layer, and then sputtering and lift-off of platinum as heating and temperature monitoring device (204 sputtered platinum, 205 P+ doped silicon, 206 thin thermal oxide); c) filling the trenches and cavities with low-evaporation oil or photoresist as sacrificial material (207 sacrificial oil/photoresist), depositing and patterning a thick layer of parylene on top (208 thick parylene) of the thermal oxide and the oil/photoresist to seal the channels and microfluidic chambers, and then patterning the oxide on the front and back side of the silicon substrate in buffered HF acid (BHF); d) releasing the sampling probe in TMAH or EDP etchant with p+ doped region for etching stop, etching oxide at the tip of the sampling probe in BHF to open the channel, and draining or dissolving the sacrificial oil/photoresist (209 exposed silicon, 210 released probe). Another PDMS layer can be cast on top of the parylene layer for additional structural strength in the microfluidic device region. Parylene-based microfluidic devices have been successfully used for on-chip PCR process (Shin) (Quach).

Microscopic pores in the lyophilized reagents obtained in the freeze drying process (Oetjen) (Rey) permit the flow of gas when suction is applied to the pipette by the precision syringe pump. The suction will pull the encapsulated cell towards the lyophilized reagents, and upon contact, will reconstitute the PCR and lysis reagents with the cell plug. At this time, the cell will become lysed and ready to undergo PCR cycling. Thermal cycling for PCR will require two high temperature steps for assisting in cell lysis (Ke), followed by 20-30 cycles of annealing and extension steps as needed for amplification. Detection of PCR will require a standard Laser induced fluorescence detector.

Figure 3:
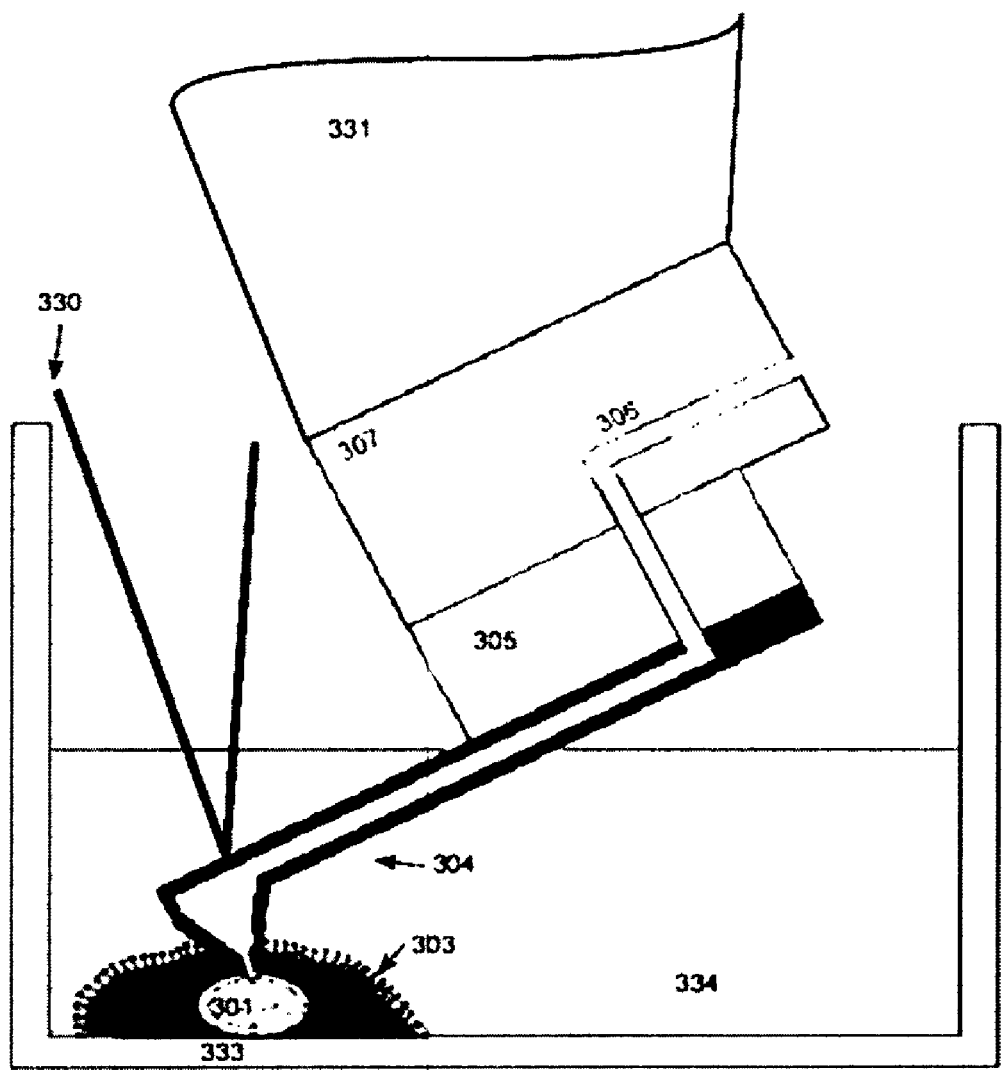
FIG. 3 illustrates a specialized AFM probe (pipette) on a microfluidic chip.

FIG. 3 illustrates a specialized AFM probe on a microfluidic chip. This device combines scanning probe microscopy (SPM) with CE to investigate single cell and nucleus biomolecules. We are proposing the development of a micromachined (MEMS) nanoscale fluidic scanning probe and scanning and analysis system with ability for imaging (morphology mapping with nanometer resolution) and low abundance biomolecule measurements of cells. The probe will allow the visualization of subcellular structure. The same probe will function as a nanoscale pipette allowing the extraction of biomolecular contents of individual nucleus or other organelles of a cell and their subsequent manipulation, labeling, separation, and quantification without the need for lysing. The probe and system will provide scientists the capabilities to track the ebb and flow of signal transduction cascades, protein-protein interactions, protein-nucleotide interactions, movement of subcellular elements within cells, and other dynamic events. For instance DNA can be extract from the nucleus of a cell without lysing. This tool will permit quantitative and real time observation and bring new levels of understanding of the molecular physiology of cells, as well as the manner in which this physiology is affected by disease, pharmacologic agents, development, and other factors, overcoming limitations of other techniques such as having to remove the cell from its environment and surrounding cells for analysis. FIG. 3 shows a 301 nucleus in the 302 cytoplasm. The 303 cell membrane is penetrated by a 304 nano probe with hollow tip. The material is extracted and flows through the 305 probe chip via a 306 fluidic transport channel. The probe is held by the 307 probe holder with fluidic channel. A 330 laser light for probe movement tracking is reflected on the cantilever's backside. The probe can be controlled with a 331 AFM XYZ piezo for probe movement. A 333 glass slide and below inverted microscope with florescent can be used to view the cell and probe. The probe and cell are in a 334 buffer solution.

This highly sensitive detection system to measure the concentration of low abundance biomolecules such as DNA (<1000 molecules/cell) inside the nucleus of a single cell. Low abundance biomolecules are difficult to detect with the current diagnosis methods such as enzyme-linked immunosorbent assays (ELISA). This is achieved using a cantilever hollow probe with a nanometer size opening at the sharp tip integrated with a capillary electrophoresis (CE) system. The probe operates in aqueous environments and includes a microfluidic channel through the cantilever. The probe allows for extraction of biomolecules directly from an organelle through a sub-100 nm size hole on the probe tip into the microfluidic channel. Using an atomic force microscope (AFM or scanning probe microscope—SPM) contact can be achieved with direct control of applied forces reducing the potential damage to the cell or the nucleus. High resolution imaging and sub-cellular elastography can also be achieved. This system can provide sensitive, inexpensive, fast detection of low abundance biomolecules for cellular analysis, cancer biomarker detection, and drug development.

Figure 4:
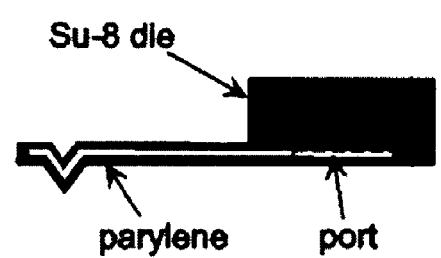
FIG. 4 illustrates the fabrication of the lab-on-a-pipette with parylene probes (pipettes) on a Su-8 substrate.
Figure 4:
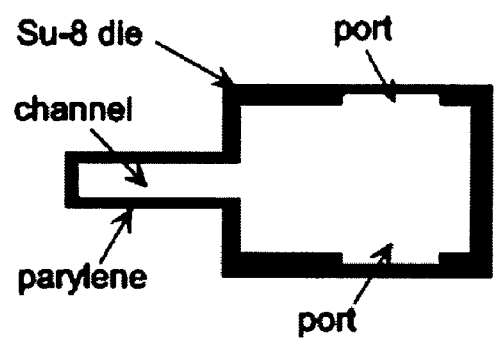
Figure 4:
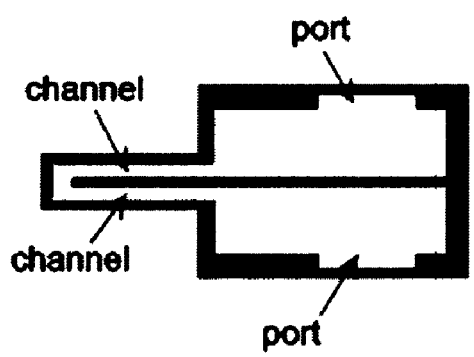
Figure 4:
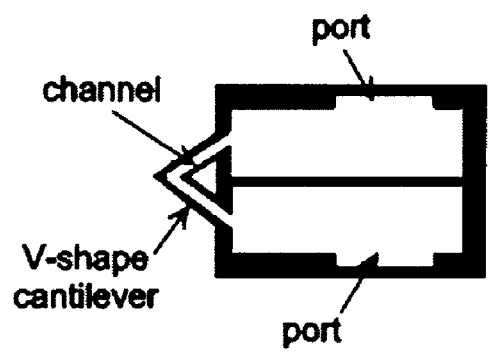

FIG. 4, shows preliminary designs. The entire cantilever structure is made of parylene and the substrate for mounting the device to AFM is made of Su-8. There are multiple shapes and channels. FIG. 8 shows some of the designs. The size of the rectangular shape cantilever is about 100 µm wide and 200 µm long; the size of the V-shape cantilever is about 100-150 µm wide.

Figure 5:
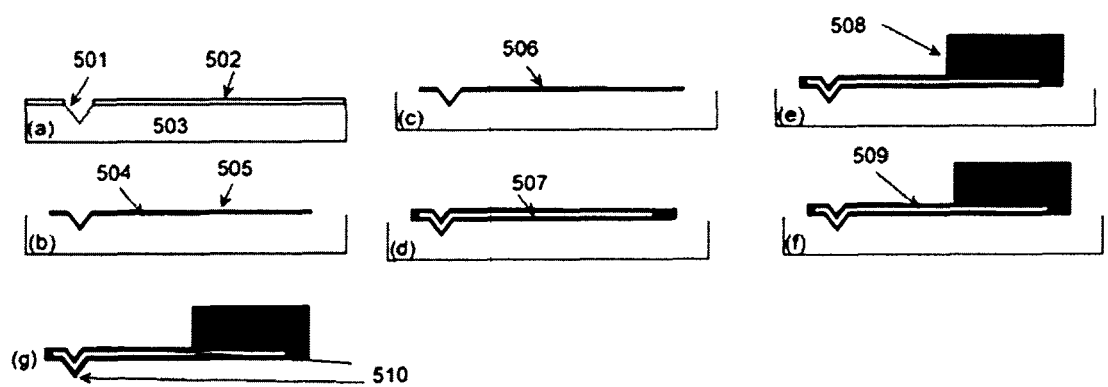
FIG. 5 illustrates an additional micro-fabrication process for fabrication the pipette of the lab-on-a-pipette system.

FIG. 5 shows a fabrication process. For AFM usage a thin metal layer is needed in order to reflect the laser beam. A nanoscale size hole at the tip will be made by focused ion beam (FIB) at the tip. The fabrication processes involves: a) forming a notch on silicon and growing oxide for oxide sharpening; b) deposition of titanium, which will act as a sacrificial layer and the first layer of parylene; c) deposition of secondary sacrificial layer; d) deposition of a second layer of parylene; e) deposition of handling chip made of SU-8; f) removal of bottom sacrificial layer and of sacrificial layer in the channel; g). FIB to make hole and metal deposition on the back-side. Enhanced designs include micro pillar arrays to support the large diaphragm or long walls to isolate the channel. 501 SiO2 tip is formed and sharpened and 502 silicon oxide is grown on the 503 Si substrate. 504 Ti is deposited as sacrificial layer and on top 505 polymer to form the first part of the pipette, then a 506 sacrificial layer is deposited that will later on be removed to form the hollow part of the pipette and another layer of 507 polymer is patterned and deposited to form the top part of the pipette. 508 Su-8 is posited to form the body of the chip. Then 509 sacrificial layer is removed. 510 FIB is used to make a hole and metal is deposited on the backside for reflectance.

An alternative fabrication process entails attaching a commercially available pipette on a substrate and fabricating the microfluidic chip described previously on the substrate. Yet another fabrication process includes bonding of two silicon wafers or one silicon and one glass wafer, where the pipette is included on the design and one wafer includes the microfluidic chip.

A lab-on-a-pipette device may also be used for fluorescence in-situ hybridization (FISH). A lab-on-a-pipette can be used for low-copy-number biomolecule (<1000 molecules/cell) detection of any type of biomolecule including proteins etc. On-chip FISH provides higher throughput and cost reduction compared to conventional FISH. FISH techniques can also be integrated on a chip with a pipette.

The lab-on-a-pipette device can be used with a scanning system. For example, a motorized or a piezoelectric stage or a combination may be used to control and move the device and/or the sample. The device can also be used with an atomic force microscope (AFM) or scanning probe microscope (SPM) as an AFM or SPM scanning probe (cantilever) allowing for topography as well as other measurements afm type of measurements. The pipette can be fabricated using conventional cantilever fabrication techniques and it includes a hollow area within the cantilever with an opening on one side at the tip and on the other side to the micro-fluidic analysis system.

The pipette (or hollow tip or hollow cantilever or hollow probe) may include an integrated heater at the end of it. The heater may be used for penetrating the zona pellucid or other purposes. An integrated heater may be included in other parts of the pipette or the fluidic system to create a fluidic flow.

One advantage of this device is that it performs SCA in a picoliter container, which represents a $10^3$ to $10^6$ fold reduction over conventional techniques. Such a drastic reduction of volume can substantially improve PCR sensitivity (and other protocols) by increasing the effective sample concentration. Performing SCA in small volumes will have transformative impact in both SCA and PGD. Single cell genomic analysis is a critical enabling technology for PGD, mutation analysis in oncology, and other areas. For single gene analysis, maybe the PCR reaction will be carried out on-chip as shown, filling the need for a low-cost, singular diagnostic. For multiplexed genetic analysis, the on-chip system described may be used to perform whole genome amplification (WGA), and the amplified DNA will then be handed off to next generation sequencing instruments which can quantify the entire genome. Carrying out the critical 'pre-amplification' step on-chip in a low-volume, isolated environment will reduce contamination and improve accuracy of the subsequent analyses. Accuracy is a key challenge in PGD.

Microfluidic devices to detect/measure proteins and other biomolecules have been described in prior art, for instance with fluorescent-antibody binding. This invention combines existing microfluidic chips with micro-aspiration needles/pipettes into one device.

The device can be used to detect for example disorders like cystic fibrosis, Charcot-Marie-Tooth neuropathy, haemophilia A, breast cancer, lung cancer, prostate cancer and other types of cancer. It may also be used to detect and measure the concentration of various analytes in blood such as concretion of drugs like heparin. The device may be used for in serum-based diagnosis to extract blood and isolate, detect, amplify, and analyze specific cells such as circulating tumor cells (CTCs) that circulate in the bloodstream. The device may also be used to analyze cell membrane, organelles, and ion channels on the membrane of the cell.

Chip clogging and pressure requirements are common in microfluidics, but have been addressed: for example, reliable fluidic interconnects are now commercially available and batch-manufactured chips can be easily replaced when clogged. Low-cost prototyping methods can be used to test microfluidic designs with <1 day turnaround.

The microfluidic analysis module may also include a platform technology for the detection low abundance biomolecules such as an array of microcantilevers with embedded piezoresistive sensors in a microfluidic chip. Micromachined cantilever arrays coated with specific antibodies include embedded piezoresistive sensors to identify an analyte by measuring the change of resistance of the sensor caused by the bending of the cantilevers. The chemo-mechanical bending of the cantilever is mainly due to the surface stress generated from analyte adsorption or binding with the coated receptors. The cantilevers can be coated with the desired receptors to bind proteins, peptides or micro RNAs. Several additions and aspects may included: 1) use of parylene to fabricate the cantilevers with at least ×10 higher sensitivity, 2) reduction of cantilever size to micron and submicron dimensions, 3) ultra thin metallic piezoresistive films increase sensitivity and eliminate the need of the atomic force microscopy optical detection system, 4) address non-specific binding and noise using a combination of strategies including a reference cantilever. The benefits of the cantilever system integration are: 1. Platform for label free assay of biomolecules. While the sensing mechanism of the cantilever is based on either stress/strain change (in defection) or mass/frequency change (in resonant mode), florescent label for detection optical system is not necessary. This enables a portable integrated system. 2. Operation in the presence of serum proteins. Previously cantilevers could not be used in the presence of serum proteins because the signal from non-specific adsorption of serum proteins was greater than the signal from the biochemical of interest. Superhydrophobic textures designed on the cantilever surfaces and chemical modification can help prevent non-specific adsorption. In addition, other cantilevers use laser detection which does not function well in serum blood. 3. High sensitivity. High sensitivity can be achieved by using parylene cantilevers advancing the sensing limits to detect low abundance biomolecules. 4. Scalability/throughput. The device can be scaled to measure concentrations of different analytes by having a number of cantilevers in an array or a number of wells each with a cantilever coated with relevant antibodies. 5. Minimum sample preparation. Operation in the presence of ambient proteins and absence of biofouling means the devices will not require prior separation of proteins. 6. High Speed. The analysis time is on the order of several minutes and is determined by the flow rate of the serum over the cantilever probes for close contact and the diffusion time of the proteins to reach the binding reagents. Compared with ELISA that requires labeling using an enzyme to elicit a chromogenic or fluorogenic or electrochemical signal, this technique is rapid and detection can be done at any location. 8. Low cost. The unit cost of the device is relatively low as the devices can be batch-produced reliably and inexpensively. Further, because the device is label free, reagent costs are limited to the cost of purchasing antibodies for capturing target biomolecules. 9. Real-time monitoring. The binding process between the antibodies and antigens can be monitored real-time as opposed to competing techniques s.a. ELISA. 10. Portability/miniaturization: for example a 20×20 array of cantilevers (400 cantilevers) can easily fit in 10 mm×10 mm area while all of the electronic components fit on a low power chip.

An integrated 'lab-on-a-pipette' will provide "sample-to-answer" single cell genetic diagnosis for preimplantation genetic diagnosis (PGD) and other forms of single cell analysis (SCA). The 'lab-on-a-pipette' device integrates a microaspiration tip with microfluidic analysis components to conduct in-situ, real-time single cell genetic diagnosis in a single device. The microaspiration tip will extract and encapsulate a cell into an ultra-low volume plug (<1 nL). The microfluidic analysis module with embedded lyophilized reagents will perform cell lysis, PCR amplification, and optionally real time fluorescence analysis. This solution is novel and yet builds upon well established technologies. Microfluidic devices have been successfully used to analyze low copy biomolecules (less than 1 pg) such as DNA of a single cell. Moreover, microfluidic platforms have been able to manipulate cells and have provided extremely high detection sensitivity. However, sampling single cells has been a major challenge. This device couples micromachined aspiration tips directly to sensitive microfluidic analysis modules, providing an elegant solution to the difficult problem of single cell sampling and isolation. The device addresses major limitations of the current PGD procedures by being able to analyze small amounts of DNA, eliminating fluid transfers which cause contamination, reducing analysis time, and reducing costs. Furthermore, the small fluid volumes (pL) used in our system will increase the effective concentration and therefore provide better PCR amplification and therefore will improved accuracy in measuring single gene mutations.

The lab-on-a-pipette technology can ultimately become a versatile tool for the exploding field of single cell analysis (SCA). SCA tools are urgently needed to quantitatively record proteomic, genomic, or metabolic markers which reveal the status of the cell. Low-copy-number biomolecules (<1000 molecules/cell) have a significant function in cell operation, although they are often lost in the detection process. Small changes of concentration or altered modification patterns of disease-relevant low abundance components can be potentially used as biomarkers of different stages of disease such as cancer, in diagnosis, in monitoring the growth of the tumor, and response to the therapy. SCA is also important in studying cell mutations and in drug screening. The ultimate goal of this device is to provide a versatile platform tool for basic research, drug discovery, and clinical diagnosis of rare or localized cell populations.

Although microfluidic platforms can theoretically provide analysis in nL to pL volumes, their potential benefits often cannot be realized because it is difficult to transfer small volume samples to the chip. The device disclosed combines microfluidic diagnostics with micromachined pipettes in an integrated, automated system for in-situ diagnosis. Thus, the proposed device addresses major limitations of the current PGD procedures by being able to analyze small amounts of DNA, eliminating cell fixation and most sources of contamination (since the cell is transferred directly from the embryo to the device for analysis), and reducing costs (less people involved in genetic diagnosis, reduced procedures and time). The device disclosed can also provide fast analysis rates, a key benefit for a time-sensitive procedure like PGD. The device disclosed can complete an analysis much faster because there is no need for instance to transfer the cells to different tubes and ship the cells to a different location for analysis. In addition, amplification can be done much faster, embedded micro-heaters can heat to 100° C. in less than 10 seconds, reducing the time that it takes to complete 30 cycles to a couple of minutes from the current 10 minutes. The smaller fluid volumes in the form of plug handled by the micropipette and microfluidic device increase the effective concentration and provide better amplification with improved results and better chances of measuring single gene mutations.

The 'lab-on-a-pipette' device integrates a microaspiration tip with microfluidic analysis components to conduct in-situ, real-time single cell genetic diagnosis in a single disposable device. The microaspiration tip extracts and encapsulate a cell into an ultra-low volume plug. The microfluidic analysis module with embedded lyophilized reagents will perform cell lysis, PCR amplification, and real time fluorescence analysis. Microfluidic devices have been successfully used to analyze low copy biomolecules (less than 1 pg) such as DNA of a single cell. Moreover, microfluidic platforms have been able to manipulate cells and have provided extremely high detection sensitivity. However, sampling single cells has been a major challenge. In this invention, micromachined aspiration tips are coupled directly to sensitive microfluidic analysis modules, providing an elegant solution to the difficult problem of single cell sampling and isolation. The proposed device addresses major limitations of the current PGD procedures by being able to analyze small amounts of DNA, eliminating fluid transfers which cause contamination (the cell is transferred directly for analysis), reducing analysis time, and reducing costs (less people involved in genetic diagnosis, reduced procedures and time, elimination of expensive hardware). Furthermore, the small fluid volumes (pL) used in this system will increase the effective concentration and therefore provide better amplification and improved accuracy in measuring single gene mutations.

The fluidic system consists of a commercially available precision suction pump and micro connecting tubes that will attach to the 'lab-on-a-pipette' device. Other types of micropumps may also be used. These may be intergrated with the proposed device. A scanning system can be modified and adapted for microfluidic experimentation. The system can be equipped with a piezo scanner with a maximum XYZ scan range of 100 um×100 um×100 um and 1 nm resolution and a motorized scanner with XYZ 25 mm×25 mm×25 mm with 100 nm resolution. Peripheral devices may include an inverted optical microscope, a CCD camera, and a signal access module, which can access most real-time signals inside the system. The tip of the pipette can be placed on a coverslip or a micro-well that contains the cells. Using a micromanipulator, the pipette can be guided over a cell. Suction can be applied to extract the cell from the coverslip into the pipette.

Reagents for cell lysis and gene-specific primers for TAQ-Man PCR can be purchased. For example, TAQMan probes embedded into the lyophilized reagents can bind to genes in question, resulting in increased fluorescence if the matched gene sequence is present. The reagents can be combined appropriately, and pumped as a plug into the pipette, and lyophilized on chip. The process of lyophilization (freeze drying) of biomolecules has been extensively studied, and the effect of process parameters are well understood. Proteins and reagents have been lyophilized on chip using a freeze drying process. Lysis reagents and PCR reagents can be combined together without adverse effects on the PCR reagent. The lyophilized reagents may occupy a 300-1000 μm length within the pipette, above the microheaters. Alternatively, the reagents can be simply dried on the chip. This has been used successfully for RT-PCR amplification with RNA polymerase and other bioactive molecules.

The microheater can be formed by thin-film platinum and can also be used for temperature measurement as an RTD by monitoring the resistance change. The thermal cycling capabilities of microheater are characterized using an infrared microscope and microthermocouples. The device provides programmable temperatures between 30 and 100° C., and have accuracy of 1° C., and thermal time constants <500 ms. PCR cycling can also be performed using an external laser. IR lasers are available with several watts power, and can bring their illuminated region to >100° C., well higher than what is needed for PCR cycling.

Microscopic pores in the lyophilized reagents obtained in the freeze drying process permit the flow of gas when suction is applied to the pipette by the precision syringe pump. The suction pulls the encapsulated cell towards the lyophilized reagents, and upon contact, will reconstitute the PCR and lysis reagents with the cell plug. At this time, the cell will become lysed and ready to undergo PCR cycling. Thermal cycling for PCR will require two high temperature steps for assisting in cell lysis, followed by 20-30 cycles of annealing and extension steps as needed for amplification The lyophilized reagents can also be placed in a small cavity outside the primary channel.

Detection of PCR requires a standard Laser induced fluorescence detector. A low cost 405 nm laser diode which provides up to 50 mW optical power can be used. The dichroic mirror, excitation, and emission filters will be obtained from commercially. Using a 40× objective, the light can be focused on the capillary where the reagents and microheater are located.

Cells can be aspirated into the pipette in a 300 pL plug, reconstituted with the on-chip reagents, and thermally cycled. Typical temperature cycling conditions are 94° C., 55° C., and 72° C. for denaturing, annealing, and extension, respectively. Whole genome amplification reagents can be commercially obtained similarly generic intercalating dyes to measure the DNA concentrations during the PCR cycling can also be purchased from vendors. The reagents may include primers and probes for testing.

The features and advantages of the present invention described in the embodiments are presented for illustrative purposes only and should not be construed to limit the scope of the invention. Many modifications and variations of these embodiments are possible. To illustrate, one can shrink the dimensions of the device to submicron features or smaller to nano-pipettes. One or two or all three dimensions may be in the submicron range.

While the invention has been thus been described with reference to the embodiments, it will be readily understood by those skilled in the art that equivalents may be substituted for the various elements and modifications made without departing from the spirit and scope of the invention. It is to be understood that all technical and scientific terms used in the present invention have the same meaning as commonly understood by one of ordinary skill in the art to which this invention belongs.

The apparatus comprises of a pipette (or otherwise called hollow cantilever or probe or hollow structure etc.) and a microfluidic component. The microfluidic component may be used for single cell analysis. A positioning device can be used to manipulate the apparatus in contact with an analyte. The sample can be a cell and the analytes can be cellular biomolecules such as DNA or proteins. The analyte can be a cell, an organelle, the membrane of a cell, or a channel on the membrane of a cell. The fluidic module may include temperature controlled chambers. The fluidic module may include an optical analysis chamber and chambers for mixing the sample with dried or liquid reagents. The apparatus may also have an element to control fluid motion such as a pump. The hollow structure may include an element for sensing movement or an element for moving the hollow structure. The elongated hollow structure may include a heater. The fluidic module may include components to perform cell lysis and polymerase chain reaction amplification. The fluidic module may include components to perform real time fluorescence analysis. In general this apparatus can be used as follows: positioning the hollow pipette with an opening near an analyte, bringing the analyte through the opening into the channel, moving the analyte through the channel into a fluidic unit connected to the channel, performing processes to the analyte in the fluidic unit, and detecting the analyte. The analyte can be a single cell that is encapsulated in a liquid plug with analysis reagent, and the fluidic unit may include a lysis component to lyse the cell and a thermal cycling component to amplify certain predetermined macromolecules of the cell. The fluidic unit may include an analysis component to analyze and read the results using optical or electrochemical detection.

REFERENCES

1). Andersson, van den Berg. "Microtechnologies and nano-technologies for single-cell analysis." Current opinion in biotechnology (2004): vol. 15, pp. 44-49. 2) Anselmetti. "Single Cell Analysis: Technologies and Applications." John Wiley and Sons (2009): 258. 3) Carson. "Trophectoderm Microbiopsy in Murine Blastocysts: Comparison of Four Methods." Journal of Assisted Reproduction and Genetics (1993): Vol. 10, No. 6, 427. 4) Clement-Sengewald, A, Buchholz, T, Schutze, K, et al. "Noncontact, laser-mediated extraction of polar bodies for prefertilization genetic diagnosis." J Assist Reprod Genet (2002): 19:183. 5) Errington, Stohr, Heers, Lees. "The Investigational Anti-convulsant Lacosamide Selectively Enhances Slow Inactivation of Voltage-Gated Sodium Channels." Molecular Pharmacology (2008): vol. 73 no. 1 157-169. 6) EU. "Ban on animal testing." http://ec.europa.eu/enterprise/sectors/cosmetics/animal-testing/(2010). 7) Fukuyama, Mitsudomi, Sugio, Ishida, Akazawa, Sugimachi. "K-ras and p53 mutations are an independent unfavourable prognostic indicator in patients with non-small-cell lung cancer." Br J Cancer (1997): 75(8), 1125-1130. 8) Garcia, E. et al. "Controlled microfluidic reconstitution of functional protein from an anhydrous storage depot." Lab on a Chip (2004): 4(1), 78-82. 9) Gleicher, N, Weghofer, A, Barad, D. "Pre-implantation genetic screening: "established" and ready for prime time?" Fertil Steril (2008): 89:780. 10) Goldberg, Carey. "In vitro field facing slowdown." Boston Globe (Nov. 14, 2005). 11) Gulliksen, A. et al. "Storage and reactivation of enzymes in a disposable, selfcontained Lab-on-a-chip system." In Proc. Micro Total Analysis Systems. (2007). 12) Gygi, Rist, Griffin, Eng, Aebersold. "Proteome Analysis of Low-Abundance Proteins Using Multi-dimensional Chromatography and Isotope-Coded Affinity Tags." Journal of Proteome Research (2002): 1 (1), pp 47-54. 13) Handyside, A H, Kontogianni, E H, Hardy, K, Winston, R M. "Pregnancies from biopsied human preimplantation embryos sexed by Y-specific DNA amplification." Nature (1990): 344:768. 14) Handyside, A H, Pattinson, J K, Penketh, R J, et al. "Biopsy of human preimplantation embryos and sexing by DNA amplification." Lancet (1989): 1:347. 15) Huang, et al. "Counting Low-Copy Number Proteins in a Single Cell." SCIENCE (5 Jan. 2007): VOL 315 5 81. 16) Hui, Bhatia. "Silicon Microchips for Manipulating Cell-cell Interaction." J V is Exp. (2007): (7): 268. 17) Iacopetta, Grieu, Powell, Soong, McCaul, Seshadri. "Analysis of p53 gene mutation by polymerase chain reaction-single strand conformation polymorphism provides independent prognostic information in node-negative breast cancer." Clinical Cancer Research (1998): 4; 1597. 18) Jeanine Cieslak-Janzen, et al. "Multiple micromanipulations for preimplantation genetic diagnosis do not affect embryo development to the blastocyst stage." Fertility and Sterility (2006): Vol. 85 No. 6 1826. 189, C. et al. "Single step cell lysis/PCR detection of Escherichia coli in an independently controllable silicon microreactor." Sensors and Actuators B: Chemical (2007): 120(2), 538-544. 20) Langeslag, Moolenaar. "Activation of TRPM7 channels by phospholipase C-coupled receptor agonists." Journal of Biological Chemistry (2007). 21) Lee, Park, Yang, Chung, Yoon, Kim, Kim, Kim. "Bulk-micromachined submicroliter-volume PCR chip with very rapid thermal response and low power consumption." Lab on a Chip (2004): vol. 4, pp. 401-407. 22) Liu, et al. "Self-contained, Integrated Biochip System for Sample-to-Answer Genetic Assays."7th International Conference on Miniaturized Chemical and Biochemical Analysts Systems (2003): 1319. 23) Liu, Robin H., Grodzinski, Piotr. "Fully Integrated Microfluidic Device for Direct Sample-to-Answer Genetic Analysis." Microarrays, Integrated Analytical Systems (2009): p. 37. 24) Mamin, H. J. "Thermal writing using a heated atomic force microscope tip." Applied Physics Letters (1996): 69, 433. 25) Marcus, et al. "Microfluidic Single-Cell mRNA Isolation and Analysis." Analytical Chemistry (Mar. 31, 2006): 5.4. 26) Maruvada, Wang, Wagner, Srivastava. "Biomarkers in molecular medicine: cancer detection and diagnosis." BioTechniques Biomarkers in Cancer Research (2005): 38:S9-S15. 27)

Nagai, Murakami, Morita, Yokoyama, Tamiya. "Development of A Microchamber Array for Picoliter PCR." Analytical Chemistry (2001): vol. 73, 1043-1047. 28) Oda, Strausbauch, Huhmer, Borson, Jurrens, Craighead, Wettstein, Eckloff, Kline, Landers. "Infrared-Mediated Thermocycling for Ultrafast Polymerase Chain Reaction Amplification of DNA." Analytical Chemistry (1998): c, vol. 70, pp. 4361-4368. 29) Oetjen, G. W., Haseley, P. Freeze-drying, Vch Verlagsgesellschaft Mbh. (2004). 30) Piyamongkol, et al. "Detailed investigation of factors influencing amplification efficiency and allele drop-out in single cell PCR: implications for preimplantation genetic diagnosis." Mol. Hum. Reprod. (2003): 9(7), 411-420. 31) Quach, Tai. "A Thermally Improved Quantitative PCR Chip." Tech. Digest Hilton Head (2008): 264-267. 32) Rechitsky, et al. "Reliability of preimplantation diagnosis for single gene disorders." Molecular and Cellular Endocrinology (2001): 183 S65-S68. 33) Rey, L., May, J. C. "Freeze-drying/lyophilization of pharmaceutical and biological products." Informa Healthcare http://books.google.com/(2004). 34) SCIENTIFIC, IRVINE. "In-vitro Fertilization Procedural Manual." IRVINE SCIENTIFIC (www.irvinesci.com/techinfo/docs/IVF_manual_40833_Rev0.pdf) (2009): 5-12. 35) Seetharam, R. et al. "Long-term storage of bionanodevices by freezing and lyophilization." Lab on a Chip (2006): 6(9), 1239-1242. 36) Shin, Cho, Lim, Chung, Park, Chung, Han, Chang. "PDMS-based micro PCR chip with Parylene coating." J. Micromech. Microeng. (2003): 768-774, 13. 37) Shulman, Lee P. "Preimplantation genetic testing and diagnosis." www.uptodate.com (May 11, 2009). 38) Thornhill, et al. "ESHRE PGD Consortium 'Best practice guidelines for clinical preimplantation genetic diagnosis (PGD) and preimplantation genetic screening (PGS)'." Human Reproduction (2005): Vol. 20, No. 1 pp. 35-48. 38) Velilla, E, Escudero, T, Munne, S. "Blastomere fixation techniques and risk of misdiagnosis for preimplantation genetic diagnosis of aneuploidy." Reprod Biomed Online (2002): 4:210. 39) Yap, Christine. "PREIMPLANTATION GENETIC DIAGNOSIS." http://www.bioethics-singapore.org/uploadfile/21851%20PMAnnex%20C-7%20Dr%20Christine%20Yap-PGD.pdf (July 2003): C-7-1. 40) Ying, Liming. "Single molecule biology: Coming of age." Mol. BioSyst. (2007): 3, 377-380. 41) Zhang, L. et al. "Whole genome amplification from a single cell: implications for genetic analysis." Proceedings of the National Academy of Sciences (1992): 89(13), 5847.

What is claimed is:

1. An apparatus used to for analyzing analyze a cell or parts of a cell, the apparatus comprising of:
   a pipette comprising a micromachined elongated hollow structure with an opening at the distal end and at least one microfluidic chamber at the proximal end and wherein said chamber comprises embedded lyophilized reagents;
   a detection system comprising a camera and an optical microscope to monitor the micromachined elongated hollow structure;
   a micromanipulator attached externally to said chamber;
   said chamber further comprising a platinum thin-film microheater and temperature sensor wherein said platinum thin-film heater provides programmable temperatures between 30 and 100 degrees Celsius with an accuracy of 1 degree Celsius, and a thermal time constant less than or equal to 500 milliseconds;
   a micro-pump connected to said chamber via a micro connecting tube; and
   an element to detect movement of said elongated hollow structure wherein said element is selected from the group consisting of piezoresistive element and piezoelectric element and wherein said movement of said elongated hollow structure is selected from the group consisting of: up and down movement of said elongated hollow structure, left and right movement of said elongated hollow structure, Z-axis movement of said elongated hollow structure for imaging a surface, Z-axis movement of said elongated hollow structure for determining contact and contact pressure with a surface, Z-axis movement of said elongated hollow structure for measuring the elasticity and the stiffness of a surface.

* * * * *